United States Patent [19]

Lapidus et al.

[11] 4,104,021

[45] Aug. 1, 1978

[54] PROCESS FOR DYEING HAIR IN WHICH THE DEPTH OF SHADE IS GRADUALLY INCREASED IN SUCCESSIVE TREATMENTS

[75] Inventors: Herbert Lapidus, Ridgefield; Albert Shansky, Norwalk, both of Conn.

[73] Assignee: Combe Incorporated, White Plains, N.Y.

[21] Appl. No.: 789,076

[22] Filed: Apr. 20, 1977

Related U.S. Application Data

[63] Continuation-in-part of Ser. No. 690,885, May 28, 1976, abandoned.

[51] Int. Cl.$^2$ .......................... A61K 7/12; A61K 7/13
[52] U.S. Cl. ........................................ 8/10.2; 8/10.1; 8/11; 8/54
[58] Field of Search ............................ 8/11, 10.2, 10.1

[56] References Cited

U.S. PATENT DOCUMENTS

| | | | |
|---|---|---|---|
| 3,649,159 | 3/1972 | Cohen et al. | 8/10.2 |
| 3,920,384 | 11/1975 | Feinland et al. | 8/10.2 |
| 3,931,912 | 1/1976 | Hsiung | 222/94 |

OTHER PUBLICATIONS

"Coal Tar Hair Dyes"–News Item in Washington Post, Dec. 15, 1977.
Corbett, J. F. in Venkataramans's "The Chemistry of Synthetic Dyes", vol. 5 (Academic Press, 1971), pp. 475–505.

*Primary Examiner*—A. Lionel Clingman
*Attorney, Agent, or Firm*—Bryan & Bollo

[57] ABSTRACT

Human air is dyed in successive treatments at selected intervals with oxidation colors (aromatic primary amines and aminophenols) admixed in each treatment with an oxidizing agent ($H_2O_2$ or a derivative thereof) — the quantity of oxidation colorant applied in each treatment being substantially the same and the quantity of oxidizing agent being increased from the first to the last treatment to effect a gradual increase in depth of shade — the mixture being allowed to remain on the hair for substantially the same tine in each treatment, followed by removal by rinsing.

16 Claims, No Drawings

PROCESS FOR DYEING HAIR IN WHICH THE DEPTH OF SHADE IS GRADUALLY INCREASED IN SUCCESSIVE TREATMENTS

RELATED U.S. APPLICATION

Continuation in part of U.S. application Ser. No. 690,885, filed May 28, 1976 and now abandoned.

BACKGROUND OF THE INVENTION

1. Field of the Invention

The invention relates to an improved process for dyeing human hair, involving the production of progressively deeper colorations with succeeding treatments for attaining a target shade, and the maintenance thereof by further treatments at appropriate intervals thereafter.

2. The Prior Art

Dyeing of human hair has been effected heretofore by application of water-soluble heavy metal compounds — e.g. of Ni or Pb — together with reagents yielding a dark-colored water-insoluble metal derivative with the metal compound — e.g. pyrogallol or sulfur compounds.

A more versatile dyeing process — with which the present invention is concerned — involves application to hair of oxidizable primary aromatic amines (especially diamines) and substitution products thereof, usually together with aminophenols, in admixture with an oxidizing agent — especially $H_2O_2$ or its derivatives, such as urea peroxide, perborates, percarbonates, persulfates, perphosphates, periodates or the like — whereby socalled oxidation dyes or colors are formed in situ on the hair (cf. U.S. Pat. No. 3,649,159). While other oxidizing agents such as $FeCl_3$, iodates, permanganates or bichromates can be employed, $H_2O_2$ and its derivatives are more generally used. In the color-forming reaction, the aromatic primary amino groups and phenolic hydroxyl groups are oxidized in situ to form imino groups and CO groups, and coupling occurs to form polyimino compounds in which the aromatic nuclei assume a quinonoid configuration — e.g.

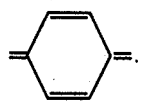

It is customary also to include in the colorant mixture, coupling compounds such as a polyhydric phenol — e.g. resorcinol, pyrogallol or the like. In general, at least a molecular equivalent or in excess thereof of the oxidizing reagent, relative to the oxidizable diamine or aminophenol, is employed, although somewhat lesser proportions of oxidant can be employed. Atmospheric oxygen can be relied upon as the sole oxidant in hair dyeing, but the use of $H_2O_2$ or its derivatives is generally preferred, since the reaction proceeds more rapidly with the latter oxidants and can be more readily controlled. Compositions yielding oxidation colors are conventionally combined with surfactants (detergents, wetting agents) and thickeners, such as are usual in shampoos, so as to facilitate removal of excess reagents by rinsing. Amine and aminophenol colorant mixtures and oxidants can be applied to hair successively in a two-step process, or they can be pre-mixed before application to the hair.

Women generally prefer a dyeing process in which the target color is attained in a single treatment — usually involving application of colorant mixture and oxidant in suitable proportions for the target color, allowing the development reaction to proceed for e.g. 15 - 60 minutes, and then washing out the excess reagents. Men, however, are usually reluctant to dye their hair in such a way that the complete color change occurs in a single treatment, since they find this embarrassing. A number of preparations have been marketed for men which gradually change or darken the color by repeated applications of the dyeing composition at selected intervals, and maintenance of the final desired coloration is effected by further applications at less frequent intervals. Such coloring compositions usually employ a heavy metal compound and a reagent adapted to form a dark colored sulfide of the metal. However, as compared with oxidation dyes, these compositions lack versatility in the hue of the available colorations.

It was known heretofore to produce gradual darkening of hair by repeated application of an oxidation color mixture at successive intervals, relying upon oxidation by atmospheric oxygen to develop the coloration (cf. U.S. Pat. No. 3,920,384). It was also known to modify the depth of shade by varying the concentration of the colorant (cf. U.S. Pat. Nos. 305,057, 1,019,576, 2,185,467, 3,128,232 and Br. Pat. No. 12,902/99), not only with oxidation color mixtures, but also with pyrogallol-Ni salt mixtures and direct dyes. Depth of shade has also been controlled by increasing the duration of the treatment, utilizing phthalaldehyde combined with an alkylolamine as the colorant mixture (cf. U.S. Pat. No. 3,871,818). Using a trihydric phenol as the colorant with an iodate, periodate or persulfate as an oxidant therefor, it was known to increase the depth of shade of the coloration produced by increasing the oxidant concentration — the oxidant and colorant being applied in the same or separate solutions (cf. U.S. Pat. No. 2,975,101).

Processes heretofore known using aromatic primary amines and aminophenols as oxidation colorants for hair do not suggest varying the proportion or concentration of the oxidant as a means for controlling depth of shade. Thus, it was known to add equal volumes of 1% and 5% solutions of a perphosphate to similar volumes of an oxidation colorant mixture (cf. U.S. Pat. No. 3,649,159), whereby however the same shade was obtained — the development time being 20 minutes in the case of the more concentrated oxidant, and 40 - 60 minutes in the case of the more dilute oxidant. No change was observed in the coloration or rate of development when 2% $H_2O_2$ or 5% $NaBO_3.H_2O$ was included with the perphosphate. U.S. Pat. No. 3,666,812 notes that increased quantities of $H_2O_2$ and $NH_3$ with oxidation colorants decolorizes the hair and produces a desired shade, but fails to suggest that deeper shades could result from an increase in the proportion of oxidant. In a process using a diaminonitrobenzene as the colorant, equal volumes of 1% and 9% $H_2O_2$ yielded shades which were similar, or in some cases, lighter in hair dyeing when the higher concentration of oxidant was employed (cf. U.S. Pat. No. 3,907,494).

OBJECTS OF THE INVENTION

It is an object of the invention to provide a process for dyeing hair with oxidation dyes in which successive applications at selected intervals first produce a predetermined light coloration, and then successively predetermined deeper shades, until a target or desired coloration is produced which can be maintained by further applications of the last applied composition at less frequent intervals.

It is a further object to provide a process as above in which the successive hair dyeing treatments can be conveniently performed by the person whose hair is to be dyed and in a short time period, in the order of 5 minutes.

A further object is to provide a hair dyeing process in which the depth of shade produced in successive treatments following the initial treatment is controlled by increasing the quantity of oxidant added starting with an amount approximately stoichiometric for the initial application and added to a substantially constant amount of colorant employed in each treatment.

DESCRIPTION OF THE INVENTION AND THE PREFERRED EMBODIMENTS

In accordance with the invention, a colorant solution is provided containing a mixture of oxidation colorants, including, for example, p-phenylenediamine, p-tolylenediamine, p-aminophenol, 2,4-diaminoanisole, and p-methylaminophenol - usually with a coupler such as resorcinol — combined with an aqueous vehicle containing, in solution, surfactants conventionally employed in shampoos, such as Na lauryl sulfate, Na-lauryl-polyethyleneglycol ether sulfate, N-lauroyl diethanolamine and ethylenediaminetetracetic acid Na salt, and alkaline reagents such as borax, morpholine and Na sulfite, which adjust the pH of the composition. A perfume can also be included. The concentration of the colorant mixture (including a coupler such as resorcinol) is advantageously from 0.5 to 8% by weight. The pH is preferably adjusted from 8 to 10. For use with such a colorant solution, there is provided an oxidant solution — especially 6% $H_2O_2$ — or equivalent solutions of $H_2O_2$ derivatives such as urea peroxide, perborate or percarbonate, persulfate or periodate.

For dyeing hair — first, in a predetermined light shade and then in successively deeper predetermined shades, a substantially constant amount of the colorant solution (suitable for moistening a head of hair uniformly) is mixed in successive treatments with a quantity of the oxidant solution which is increased in each successive treatment (e.g. 3 treatments in all) — the final treatment yielding the target or desired shade. In each case, after applying the mixture of colorant and oxidant to the hair, development of the coloration is permitted to occur over a specified period which is the same for each treatment (e.g. 5, 10 or 15 minutes). The composition is then rinsed from the hair with water. After the target shade is attained, it is maintained by re-applying the mixture used in the last treatment of the darkening series at such intervals as to color the new growth of hair in the target shade.

The process of the invention is convenient for use without professional assistance, since the user — in each treatment — has only to measure a specified constant quantity of colorant solution, mix it with a similarly measured quantity of oxidant solution — the quantities in successive treatments after the first being advantageously simple multiples of the amount used in the first application — applying the resulting mixture of colorant and oxidant to the hair, waiting a specified period — e.g. 5 minutes — and rinsing the residual mixture from the hair.

The following examples, wherein parts and percentages are by weight, illustrate the process of the invention:

EXAMPLE 1

An aqueous vehicle containing surfactants commonly employed in shampoos and pH adjusting agents is prepared having the following composition:

| | |
|---|---|
| De-ionized water | 311 parts |
| Na sulfite | 7 parts |
| Borax | 15 parts |
| Morpholine | 20 parts |
| Ethylenediaminetetracetic acid tri-Na salt | 5 parts |
| N-lauroyl diethanolamine | 35 parts |
| Na-laurylpolyethyleneglycol ether sulfate 60% | 100 parts |
| Na lauryl sulfate 30% | 200 parts |

Two colorant solutions are prepared having the following compositions — the first (A) providing light brown as the target shade, and the second (B) yielding a medium brown as the target shade:

| | A | B |
|---|---|---|
| Resorcinol | 2.5 parts | 2.5 parts |
| p-phenylenediamine | 6.0 parts | 8.0 parts |
| p-tolylenediamine sulfate | 2.0 parts | 5.0 parts |
| p-aminophenol | 3.0 parts | 6.0 parts |
| 2,4-diaminoanisole sulfate | 0.25 parts | 2.5 parts |
| p-methylaminophenol sulfate | 1.0 parts | 0.0 parts |
| Perfume (Lavender) | 5.0 parts | 5.0 parts |
| De-ionized water | 302.0 parts | 302.0 parts |
| Vehicle as above | 693.0 parts | 693.0 parts |
| Totals | 1014.75 parts | 1024.0 parts |

The resulting colorant solutions have a pH of 9.5, which promotes decomposition of $H_2O_2$ and its peroxy derivatives.

As the oxidant for use with the foregoing colorant solution, 6% (i.e, 20-volume) $H_2O_2$ is used, or an aqueous solution of an equivalent quantity of urea peroxide, Na perborate or Na percarbonate can be used — replacing — if desired — part of the water with propylene glycol to facilitate dissolution.

In use, 30 cc. of colorant solution A is mixed for the first treatment with 2.5 cc. of oxidant solution. The mixture is applied to the hair and allowed to develop for 5 minutes, a very short time period by conventional dying standards. The hair is then rinsed. The treatment yields a barely perceptible brownish coloration. After a desired interval, determined by the user (e.g. one week), a second treatment is carried out, using in this case, 5 cc. of oxidant solution with 30 cc. of colorant solution. After development for 5 minutes, the hair is rinsed, yielding an intermediate light brown shade. Again, after a desired interval of a week or so, a third application is made, using 10 l cc. of oxidant solution and 30 cc. of colorant solution. Five minutes' development, followed by rinsing, yields the final light brown target shade. This can be maintained by repeating the third treatment at such intervals (e.g. about once every 2 to 8 weeks) so as to color new growth of hair in the target shade.

Similar treatments using colorant solution B yields, first, a light brown shade, then an intermediate darker brown shade, and finally a medium brown target shade. Maintenance of the final coloration is effected in the same manner as in the case of colorant solution A.

EXAMPLE 2

Three colorant solutions are prepared having the following compositions — the first (C) yielding a medium dark brown as the target shade — the second (D), a light medium brown — and the third (E), a light brown:

| | | C | D | E |
|---|---|---|---|---|
| 1. | De-ionized water | 56.864% | 57.410% | 59.51% |
| 2. | Trisodium ethylenediaminetetracetic acid | 0.488 | 0.493 | 0.49 |
| 3. | Sodium sulfite | 0.684 | 0.690 | 0.68 |
| 4. | Borax | 1.465 | 1.478 | 1.46 |
| 5. | Morpholine | 1.953 | 1.970 | 1.94 |
| 6. | Sodium lauryl-polyethyleneglycol ether sulfate (60%) | 9.766 | 9.854 | 9.71 |
| 7. | Sodium lauryl sulfate (30%) | 19.531 | 19.709 | 19.42 |
| 8. | N-lauroyl-diethanolamide | 6.418 | 6.449 | 4.85 |
| 9. | Resorcin | 0.244 | 0.246 | 0.24 |
| 10. | Paraphenylenediamine | 0.781 | 0.591 | 0.58 |
| 11. | Para-aminophenol | 0.586 | 0.296 | 0.29 |
| 12. | Paratolylenediamine sulfate | 0.488 | 0.197 | 0.29 |
| 13. | 2,4-diaminoanisole sulfate | 0.244 | 0.25 | 0.05 |
| 13a. | Paramethylaminophenol sulfate | — | 0.099 | — |
| 14. | Perfume (lavender) | 0.488 | 0.493 | 0.49 |
| | | 100.% | 100.% | 100.% |

To prepare the foregoing colorant solutions, the water (1) is heated in a mixing kettle to 80 degr. C. 2, 3, 4 and 5 are added successively, each being completely dissolved before addition of the next. 6 and 7 are then added at the same temperature. 8 and 9 are then successively added at a temperature of 70 degr. C. 10, 11, 12 and 13 (and 13a in composition D) are added, and agitation continued for 15 minutes. The mixture is cooled to 40 degr. C. and 14 is then added.

EXAMPLE 3

Two colorant solutions are prepared having the following compositions — the first (F) yielding a light brown as the target shade — and the second (G), a medium dark brown:

| | | F | G |
|---|---|---|---|
| 1. | De-ionized water | 56.84% | 48.32 |
| 2. | Trisodium ethylenediaminetetracetic acid | 0.48 | 0.47 |
| 3. | Sodium sulfite | 0.67 | 0.66 |
| 4. | Borax | 1.44 | 1.41 |
| 5. | Monoethanolamine | 1.92 | 2.67 |
| 6. | Sodium lauryl-polyethyleneglycol ether sulfate (60%) | 9.59 | 13.39 |
| 7. | Sodium lauryl sulfate (30)% | 19.18 | 20.78 |
| 8. | N-lauroyl-diethanolamide | 5.36 | 7.29 |
| 9. | 4-chloro-resorcinol | 0.515 | 0.515 |
| 10. | Paratolylenediamine sulfate | 2.130 | 2.130 |
| 11. | Meta-aminophenol sulfate | 0.745 | 0.745 |
| 12. | Para-aminodiphenylamine sulfate | 0.650 | 0.650 |
| 13. | 2,5-diaminoanisole sulfate | — | 0.50 |
| 14. | Perfume (lavender) | 0.48 | 0.47 |
| | | 100.% | 100.% |

Colorant solutions F and G are prepared in substantially the same manner as described in Example 2.

For coloring hair, the colorant solutions of Examples 2 and 3 are applied in essentially the same manner as described in Example 1.

The quantity of oxidant employed in the first treatment as illustrated in the foregoing examples should provide 0.5 to 2 times the amount required to oxidize the aromatic primary amino groups and aminophenols contained in the components of the colorant solution. The amount of oxidant has been termed herein as "approximately stoichiometric" to dramatize and characterize the amount as being very small in contrast to the prior art. The quantity of oxidant used in the second treatment as illustrated in the examples should provide 1.0 to 4 times the amount required of oxygen to oxidize the primary aromatic amino groups and aminophenols contained in the colorant solution. In the third and subsequent maintenance treatments illustrated in the examples, the quantity of oxidant should provide 2 to 10 times the amount of oxygen required to oxidize the aromatic primary amino groups and aminophenols contained in the colorant solution employed.

In the colorant solutions illustrated in the foregoing examples, the concentration of surfactant components advantageously ranges from 10 to 25%, that of the pH adjusting components from 2 to 10%, and that of the aromatic primary aromatic amino group compounds and aminophenols (with the coupler or couplers), from 0.5 to 8%.

As illustrated in the examples, the quantities of oxidant used in the successive treatments after the first are simple multiples of the amount used in the first treatment — especially multiples constituting a geometric series (1, 2, 4) — or simple multiples (1, 2, 3, 4). A geometric series of multiples is preferred, since it yields a substantially linear darkening of the hair in attaining the target shade. In each case, the development time for each treatment of the series is substantially constant — e.g. 5, 10 or 15 minutes.

Oxidizable aromatic primary amines and aminophenols which can be used in the colorant solutions as such, or in the form of their water-soluble salts, such as sulfates, hydrochlorides or acetates — may be selected from the following:

o-, p- and m-phenylenediamine
p-aminodiphenylamine
p-aminodiphenylamine sulfonic acid
2-amino-4-nitrophenol
4-amino-2-nitrophenol
p-aminophenol
m-aminophenol
o-aminophenol
o-, m- and p-methylaminophenol
2-aminophenol-4-sulfonic acid
4-aminophenol-2-sulfonic acid
o-anisidine
2,4-diaminoanisole
2,5-diaminoanisole
p,p'-diaminodiphenylamine
p,p'-diaminodiphenylamine sulfonic acid
p,p'-diaminodiphenylmethane
1,8-diaminonaphthalene
2,4-diaminophenol
2,4-diaminophenetole
2,5-diaminophenol-4-sulfonic acid
N,N'-dimethyl-p-phenylenediamine
4,6-dinitro-2-aminophenol
N-(p-hydroxyphenyl)-glycine
N-(2-hydroxy-5-nitrophenyl)-glycine p-methylaminophenol
4-nitro-o-phenylenediamine
m- and p-tolylenediamine
2,4,6-trinitroaniline Couplers which can be used in the colorant solution are, for example, polyhydric phenols such as resorcinol, chlororesorcinols, pyrocatechol, pyrogallol and hydroquinone.

Surfactants suitable for inclusion in the colorant solution or in the oxidant solution combined therewith are, for example, higher fatty acid soaps; higher fatty alcohol sulfuric ester salts of alkali metals, ammonium or aliphatic amines; higher fatty acid alkylolamides; polyalkyleneglycols; and ethylenediamine-tetracetic acid alkali metal or ammonium salts.

Compounds suitable for adjusting the pH which can be included in the colorant solutions illustrated in the examples include alkylolamines, such as mono-, di- and triethanolamine, water-soluble alicyclic amines such as morpholine, and alkali metal salts of weak inorganic acids such as borax, alkali metal sulfites and alkali metal carbonates.

The oxidants used in the oxidant solution of the example can be derivatives of $H_2O_2$ such as urea peroxide, alkali metal perborates, -percarbonates, -perphosphates, -persulfates or -periodates, as well as $H_2O_2$ itself.

Other variations and modifications which will be obvious to those skilled in the art can be made in the foregoing examples and the above outlined modifications thereof without departing from the spirit or scope of the invention.

We claim:

1. A process for dyeing hair by application of a mixture of colorant solution of primary aromatic amines and aminophenols and an oxidant containing $H_2O_2$ or a peroxy derivative for a time period yielding color development, followed by a rinse removal of the residual mixture;

the improvement to the aforesaid process comprising:
(a) applying said colorant-oxidant mixture in successive applications to gradually get rid of the undesirable hair color, wherein
(i) the time period of application of the mixture being short, on the order of five (5) to fifteen (15) minutes and of substantially the same length for each subsequent application,
(ii) the quantity of colorant solution is suitable for moistening a head of hair uniformly, and substantially constant through all applications,
(iii) the quantity of oxidant in the mixture in the first application is 0.5 to 2 times the amount required to oxidize the primary aromatic amines and aminophenols contained in the colorant solution, and successive applications having increased quantities of oxidant above said initial quantity, ranging up to 10 times the amount required for the aforesaid oxidation;
(b) each mixture having the ability to produce an oxidation color on ordinary human hair; and
(c) each such color being a deeper shade than the preceding application, whereby the user can stop the coloration process at any desirable color attainment and thereafter maintain such color level by repeating the application with the mixture of colorant and oxidant last used.

2. A process as defined in claim 1 wherein the quantity of oxidant admixed with the colorant solution in the first treatment is 0.5 to 2 times the amount required to oxidize all of the aromatic primary amines and the aminophenols contained in the colorant solution, and ranges up to 10 times said amount in the last treatment of the series yielding a target shade.

3. A process as defined in claim 2 wherein the quantity of oxidant admixed with the colorant solution in each treatment of the series after the first is a simple multiple of the quantity employed in the first treatment.

4. A process as defined in claim 3 wherein the multiples of the quantity of oxidant employed in the successive treatments following the first constitute a geometric progression with the amount employed in the first treatment.

5. A process as defined in claim 4 wherein the quantities of oxidant employed in the successive treatments of the series are substantially in the ratio of 1, 2, and 4.

6. A process as defined in claim 1, wherein the colorant solution includes, as a coupler, a polyhydric phenol.

7. A process as defined in claim 1, wherein the colorant solution comprises a surfactant.

8. A process as defined in claim 1, wherein the oxidant is selected from the group consisting of $H_2O_2$, urea peroxide, and per-salt derivatives of $H_2O_2$.

9. A process as defined in claim 1, wherein the quantity of oxidizable aromatic primary amines and aminophenols contained in the colorant solution, together with any coupler contained therein, ranges from 0.5 to 8% by weight of the solution.

10. A process as defined in claim 1, wherein the oxidant is employed in a solution of which the concentration is equivalent in oxidizing potential to that of a solution of $H_2O_2$ of about 6% concentration.

11. A process as defined in claim 1, wherein the quantity of colorant solution employed in each treatment is about 30 cc. and the quantities of oxidant solution employed in three successive treatments are respectively 2.5, 5 and 10 cc.

12. A process as defined in claim 1, wherein the pH of the mixture applied in each of the successive treatments is within the range of 8 to 10.

13. A process as defined in claim 1, wherein the colorant solution contains 2.5 parts resorcinol, 6–8 parts p-phenylenediamine, 2–5 parts p-tolylenediamine sulfate, 3–6 parts p-aminophenol, 0.25–2.5 parts 2,4-diaminoanisole sulfate, up to 1 part p-methylaminophenol sulfate, 5 parts perfume, 7 parts Na sulfite, 15 parts borax, 20 parts morpholine, 35 parts N-lauroyl diethanolamine, 5 parts ethylenediaminetetracetic acid trisodium salt, 60 parts Na-laurylpolyethyleneglycol ether sulfate, 60 parts Na lauryl sulfate, and about 793 parts water, and the oxidizing solution is 6% $H_2O_2$.

14. A process as defined in claim 1 wherein the colorant solution contains 0.24 – 0.246 parts resorcinol, 0.58 – 0.781 parts paraphenylenediamine, 0.29 – 0.586 parts para-aminophenol, 0.197 – 0.488 parts paratolylenediamine sulfate, 0.05 – 0.244 parts 2,4-diaminoanisole sulfate, up to 0.099 parts p-methylaminophenol sulfate, 0.488 – 0.493 parts perfume, 0.68 – 0.69 parts sodium sulfite, 1.46 – 1.478 parts borax, 1.94 – 1.97 parts morpholine, 0.488 – 0.493 parts ethylenediaminetetracetic acid tri-sodium salt, 9.71 – 9.854 parts sodium laurylpolyethyleneglycol-ether sulfate (60%), 19.42 – 19.709 parts sodium lauryl sulfate (30%), 4.85 –6.449 parts N-lauroyl-diethanolamide and 56.864 – 59.51 parts water.

15. A process as defined in claim 1 wherein the colorant solution contains 0.515 parts 4-chlororesorcinol, 2.13 parts paratolylenediamine sulfate, 0.745 parts meta-aminophenol sulfate, 0.65 parts para-aminodiphenylamine sulfate, up to 0.50 parts 2.5-diaminoanisole sulfate, 0.47 – 0.48 parts perfume, 0.66 – 0.67 parts sodium sulfite, 1.41 – 1.44 parts borax, 1.92 – 2.67 parts monoethanolamine, 0.47 – 0.48 parts ethylenediamine-tetracetic acid trisodium salt, 9.59 – 13.39 parts sodium lauryl-polyethyleneglycol ether sulfate (60%), 19.18 –20.78 parts sodium lauryl sulfate (30%), 5.36 – 7.29 parts N-lauryl-diethanolamide and 48.32 – 56.84 parts water.

16. A process as defined in claim 1 in which the time period of each application of the mixture is constant.

* * * * *